United States Patent [19]

Davis et al.

[11] Patent Number: 5,604,547
[45] Date of Patent: Feb. 18, 1997

[54] ASPHERIC/ATORIC WIDE FIELD SUNGLASSES AND SAFETY EYEWEAR

[75] Inventors: John K. Davis, E. Woodstock; Richard P. Waido, W. Woodstock, both of Conn.

[73] Assignee: Gentex Optics, Inc., Carbondale, Pa.

[21] Appl. No.: 532,009

[22] Filed: Sep. 21, 1995

Related U.S. Application Data

[63] Continuation of Ser. No. 115,349, Sep. 1, 1993, abandoned.
[51] Int. Cl.⁶ .............................. G02C 7/10; G02C 7/02
[52] U.S. Cl. ................. 351/44; 351/41; 351/159
[58] Field of Search ............... 2/426, 431, 434, 2/439, 445, 447, 448, 449; 351/41, 44, 159, 168, 174, 169; 359/709, 710, 711, 712, 718

[56] References Cited

U.S. PATENT DOCUMENTS

| | | | |
|---|---|---|---|
| 4,867,550 | 9/1989 | Jannard | 351/44 |
| 4,976,530 | 12/1990 | Mackay et al. | 351/44 |
| 4,978,182 | 12/1990 | Tedesco | 351/44 |
| 5,204,700 | 4/1993 | Sansalone | 351/41 X |
| 5,208,614 | 5/1993 | Jannard | 351/41 |

*Primary Examiner*—Hung Dang
*Attorney, Agent, or Firm*—Shenier & O'Connor

[57] ABSTRACT

A sunglass or eye protector molded from suitable optical material with inner and outer surfaces, both of which are noncircular in the horizontal direction and curved in the vertical meridian to provide substantially uniform thickness throughout.

23 Claims, 13 Drawing Sheets

ASPHERIC/ATORIC WIDE FIELD SUNGLASSES AND SAFETY EYEWEAR

This application is a continuation of application Ser. No. 08/115,349 filed on Sep. 1, 1993, now abandoned.

FIELD OF THE INVENTION

The invention is in the field of eyewear and, more particularly, relates to improved sunglasses and safety glasses and method of making the same.

BACKGROUND OF THE INVENTION

There are known in the prior art sunglasses and safety eyewear intended to protect the wearer's eye against the harmful effects of sunlight, as well against flying objects and the like which might otherwise strike the wearer's eye. In general, two forms of eyewear of this type are available in the prior art. The first is a spectacle in which individual lenses are mounted in a frame. A second type is one in which a spectacle with two lenses is fabricated in one piece with an integral bridge but with separate optical axes for the lens. In both of these types, the lenses themselves are of overall spherical or toric construction.

Modern design of sunglasses and safety eyewear calls for lenses with large diameters and steeply "wrapped" configurations. With lenses of such large diameter and steep wraps, the result is a lens of non-uniform thickness which may add to the weight of the lens and result in different transmission properties across the lens in the case of absorptive lenses such as sunglasses.

Another approach is to use a face form angle wherein the optical axis is angled and the optical center is near the center of the angled lens. In this way, the true optical size is limited and a more uniform thickness is provided. While it affords a lighter weight lens with the same appearance as one having correct optical axes parallel to the line of sight, it creates prism imbalance for all angles of view.

A third class of eye protectors is the one-piece face shield type having but one optical axis passing through the optical center halfway between the eyes. The eye protector is of an overall spherical or toric surface shape. Owing to the large overall diameter of this one-piece design, maintaining uniform thickness can be an even greater problem than with two lens type glasses. This is particularly true if the lens has sufficient diameter and depth to provide protection for both eyes through an outward field of view of approximately 90 degrees or greater. To achieve such a wide field of view, a break in the curve may be employed resulting in a parting line in a molded product where the outer wrap area is of a different curve and usually not of true optical quality. Alternatively, side shields might be used. Such an arrangement, however, provides an even greater interruption of vision in the outer peripheral area of the lens.

SUMMARY OF THE INVENTION

One object of my invention is to provide improved molded sunglasses and safety eyewear and a method of making the same.

Another object of my invention is to provide improved molded sunglasses and safety eyewear which have a greater freedom of cosmetic design than is possible with methods of the prior art.

Still another object of my invention is to provide improved sunglasses and safety eyewear with relatively uniform thickness throughout without sacrificing optical performance.

A still further object of my invention is to provide improved safety lenses and eye shields with integral side protection in one continuous optical surface with an unbroken side wrap with sufficient thickness to meet safety standards and to provide high quality optics through a wide field of view.

Other and further objects of my invention will appear from the following description.

BRIEF DESCRIPTION OF THE DRAWINGS

In the accompanying drawings to which reference is made in the instant specification which is to be read in conjunction therewith and in which like reference numerals are used to indicate like parts in the various views.

DESCRIPTION OF THE PREFERRED EMBODIMENT

Figure 1:
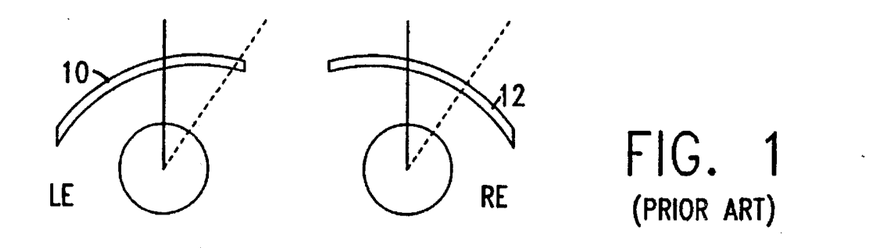
FIG. 1 is a schematic view illustrating a steeply wrapped design of the prior art.

FIG. 1 illustrates a lens of the steep "wrap" design having a horizontal curvature of approximately ten diopters. The left eye LE and right eye RE lenses are identified respectively by the reference characters 10 and 12.

Figure 2:
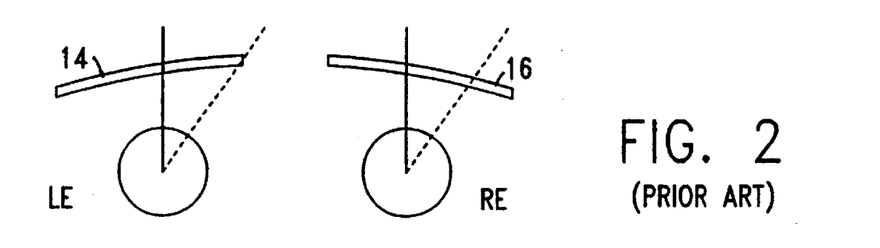
FIG. 2 is a schematic view illustrating a face form angled design of the prior art.

Other sunglasses and safety lenses have curves which are less steep than those of the lenses shown in FIG. 1. Curves of such lenses vary from as shallow as 3 or 4 diopters up to about 6.0 diopters. FIG. 2 illustrates left eye and right eye lenses 14 and 16 of this type. It will be appreciated that there are also lenses having eight or nine diopter curves between the type illustrated in FIG. 1 and the type illustrated in FIG. 2.

A subclass of the types of lenses illustrated in FIGS. 1 and 2 would be a safety spectacle or sunglass with two lenses fabricated in one piece with an integral bridge connecting the two but with separate optical axes for the lenses. The lenses themselves may have spherical or toric surfaces. A toric lens reduces bulk and permits greater style variation than does a spherical one. The optical performance and thickness of toric lenses are little different from spherical designs.

Figure 3:
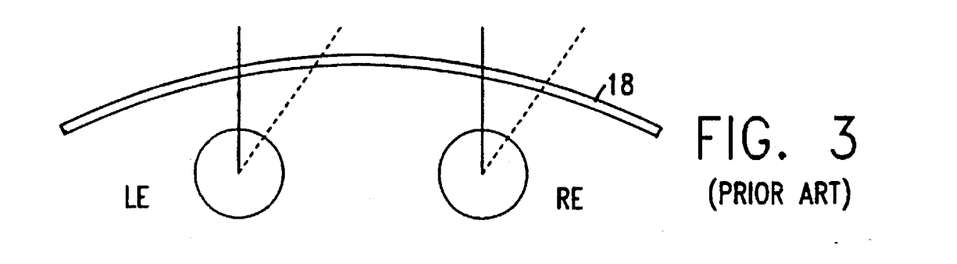
FIG. 3 is a schematic view illustrating a one-piece design of the prior art.

Yet another type of eye protector of the prior art is the one-piece face-shield type having a single optical axis passing through the optical center halfway between the two eyes. A protector 18 of this type is illustrated in FIG. 3. The surfaces of such a protector may be either spherical or toric. Maintaining uniform thickness with a protector of this type is extremely difficult. This is especially true if the lens is of a large enough diameter and great enough depth to provide protection for both eyes through an outward field of view of approximately 90 degrees or greater. Such lenses often incorporate a break in the curve or are made with side shields, as has been mentioned hereinabove.

Figure 4:
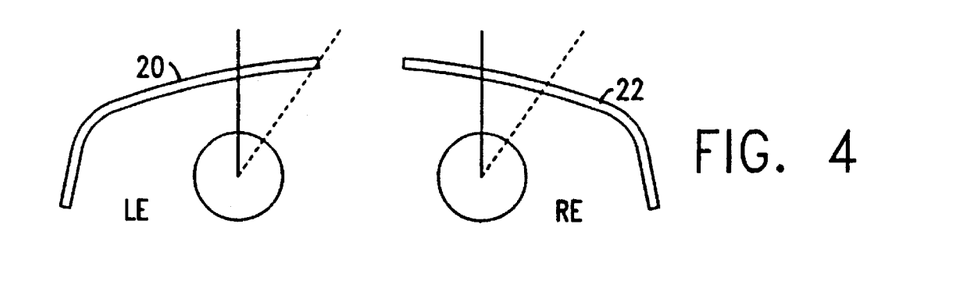
FIG. 4 is a schematic view illustrating my improved sunglasses and safety eyewear.
Figure 5:
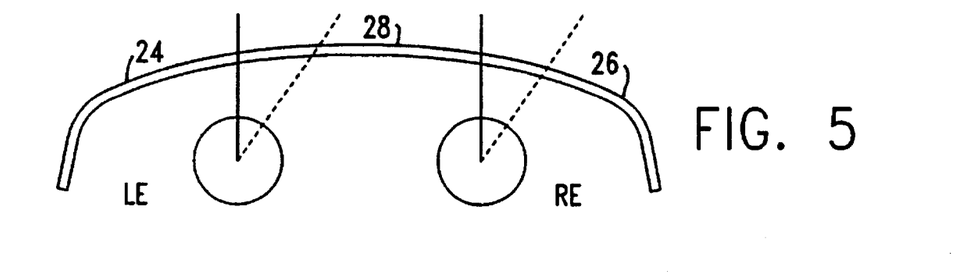
FIG. 5 is a schematic view illustrating a one-piece design of my improved sunglasses and safety eyewear.

Sunglasses or eye protectors made in accordance with my invention use aspheric and/or toric surfaces on both sides of the lenses to provide substantially uniform thickness across the entire lens. FIG. 4 illustrates the general form of left and right eye lenses 20 and 24 made in accordance with my invention. FIG. 5 illustrates a one-piece face-shield design in which left and right eye portions 24 and 26 are joined by an integral bridge 28. In lenses made in accordance with my design, as shown in FIGS. 4 and 5, the surfaces are of optical quality throughout the lens including the wrap area. My method may be used to design and produce "lens blanks" from which there may be cut a variety of cosmetic shapes. My method reduces weight and bulk while maintaining optics comparable to or superior to conventional lenses of the same general type.

Figure 6:
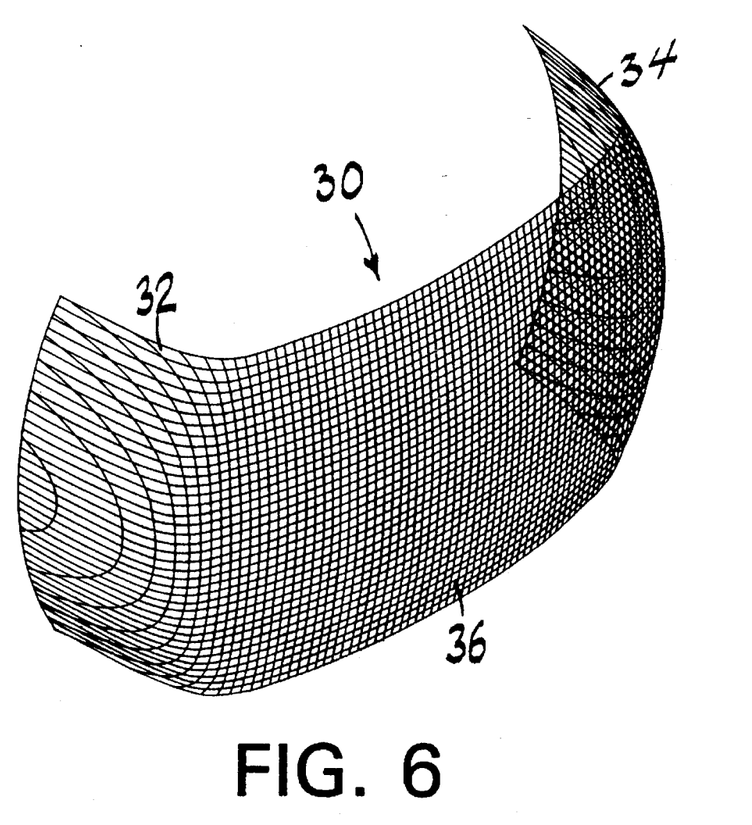
FIG. 6 is a perspective of one specific embodiment of my improved sunglass or safety eyewear blank.
Figure 7:
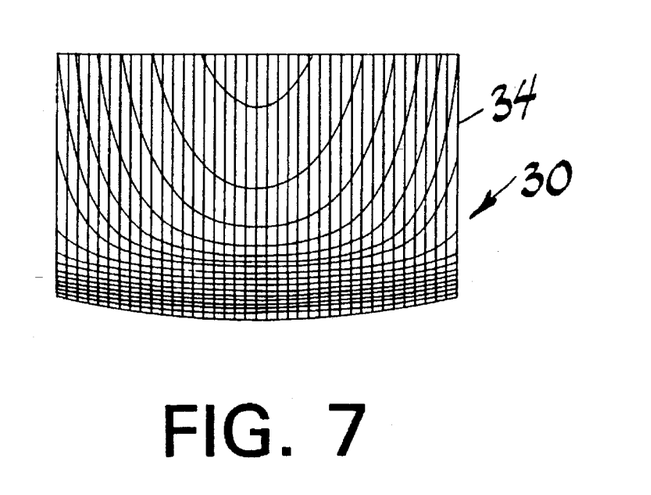
FIG. 7 is a side elevation of the blank illustrated in FIG. 6.
Figure 8:
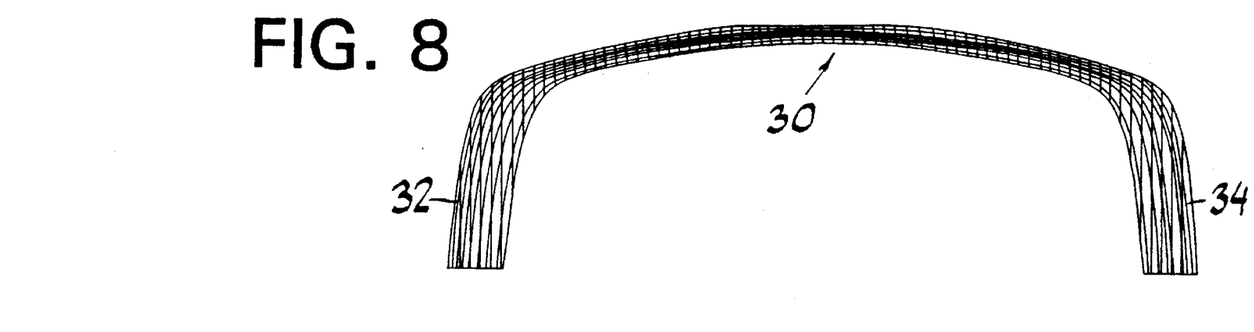
FIG. 8 is a top plan of the blank illustrated in FIG. 6.
Figure 9:
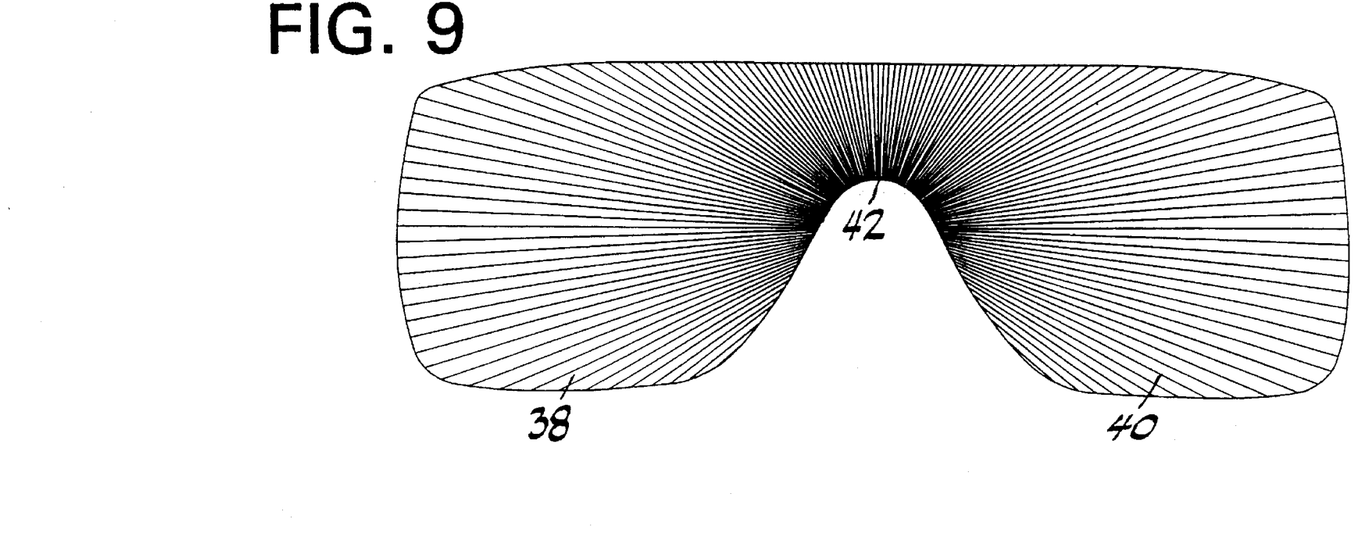
FIG. 9 is a front elevation of the blank illustrated in FIG. 6.
Figure 10:
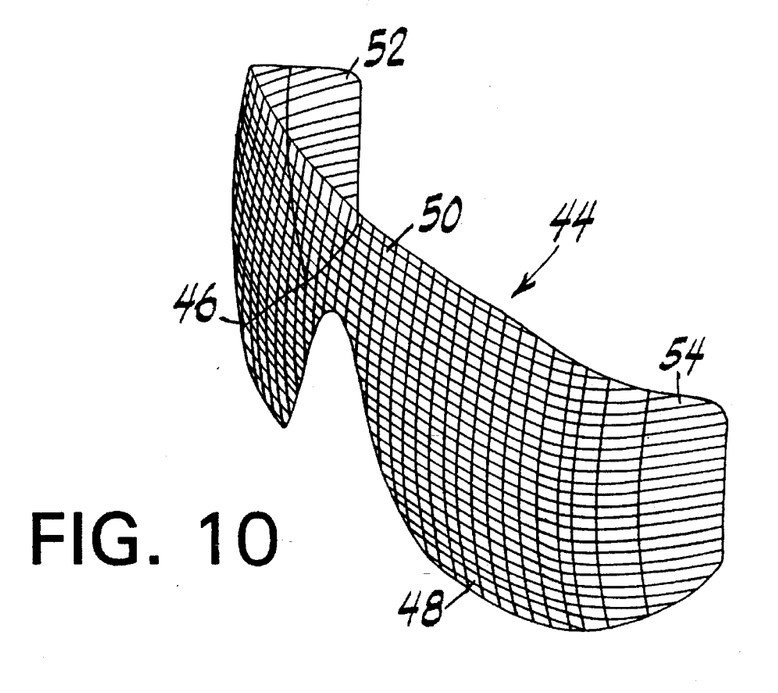
FIG. 10 is a perspective of another specific embodiment of my sunglass or protective blank.
Figure 11:
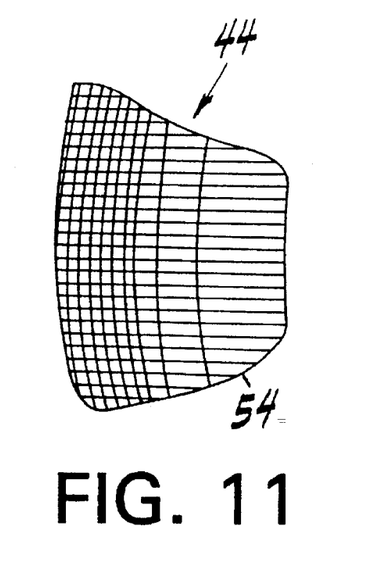
FIG. 11 is a side elevation of the blank illustrated in FIG. 10.
Figure 12:
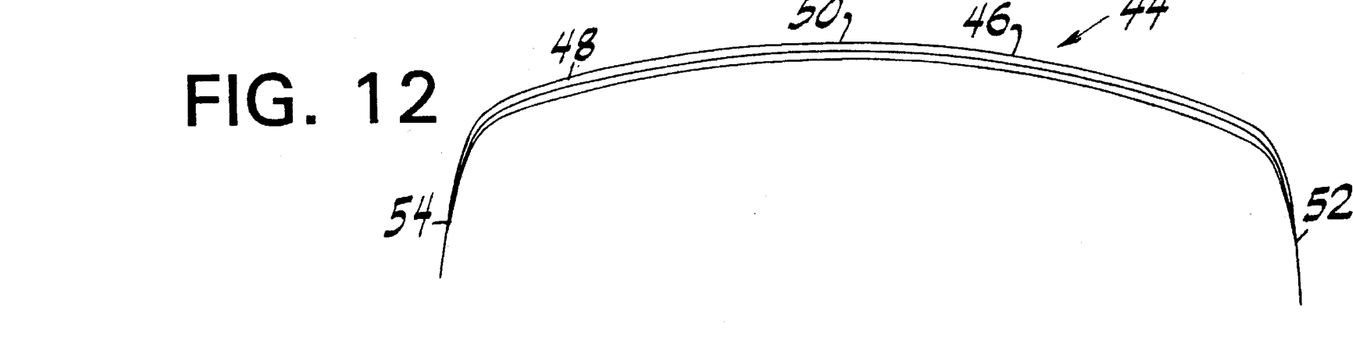
FIG. 12 is a top plan of the blank illustrated in FIG. 10.
Figure 13:
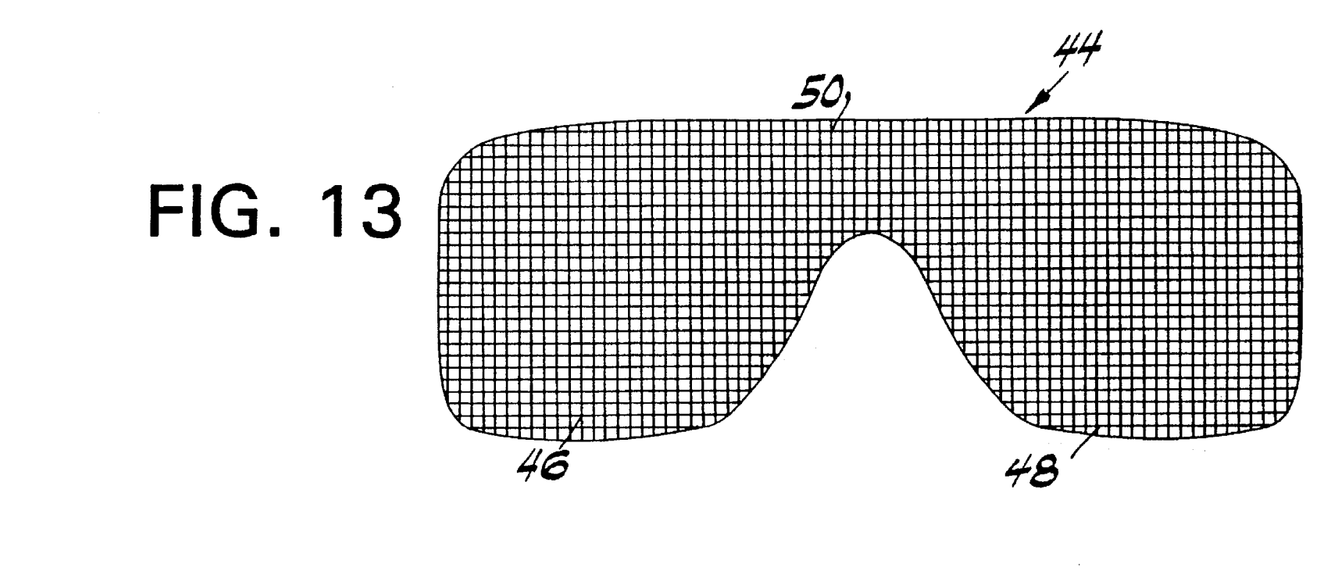
FIG. 13 is a front elevation of the blank illustrated in FIG. 10.

FIGS. 6 to 9 show a specific embodiment of a sunglass or eye protector made in accordance with my invention. FIGS. 6 to 8 show the blank indicated generally by the reference character 30 having deeper side portions 32 and 34 and a central portion 36. FIG. 9 illustrates the blank after it has been cut to form right and left lens portions 38 and 40 and a nose piece 42.

The protector illustrated in FIGS. 6 to 9 has a horizontal width of 144 millimeters and a wrap depth of 35 millimeters from the front vertex. FIGS. 6 to 9 show a bi-aspheric figure of revolution. The same horizontal cross-section could be obtained with a lens which is aspheric non-circular configuration in the horizontal and a simple circle in the vertical. This can be termed an atoric.

FIGS. 10 to 13 illustrate another specific embodiment indicated generally by the reference character 44 produced in accordance with my invention. The sunglass or eye protector 44 is formed with right and left eye portions 46 and 48 connected by an integral bridge 50 and 52. Right and left deep wrap side portions 52 and 54 extend rearwardly from the outer edges of the eye portions 46 and 48.

The protector 44 illustrated in FIGS. 10 to 13 has the same horizontal cross-section as does the protector 30 illustrated in FIGS. 6 to 9. However, the vertical curve of the protector 44 is a circle of the same central curve as the aspheric. It will be appreciated, however, that it could be different.

Figure 14:
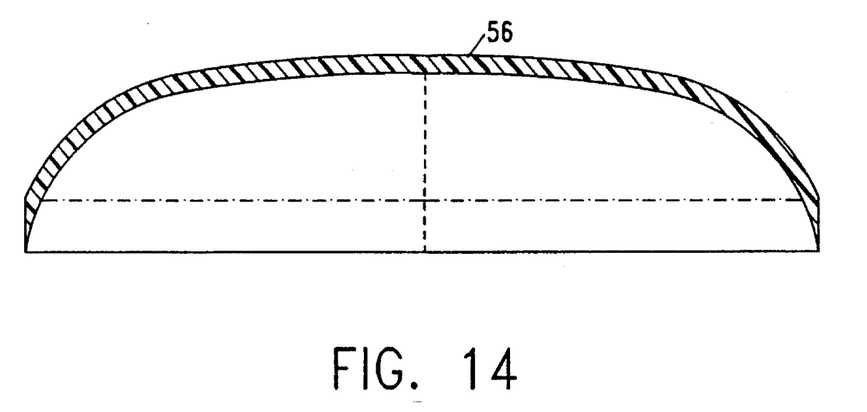
FIG. 14 is a cross-section of another specific embodiment of my improved aspheric sunglass or protective wear blank produced in accordance with my method.
Figure 15:
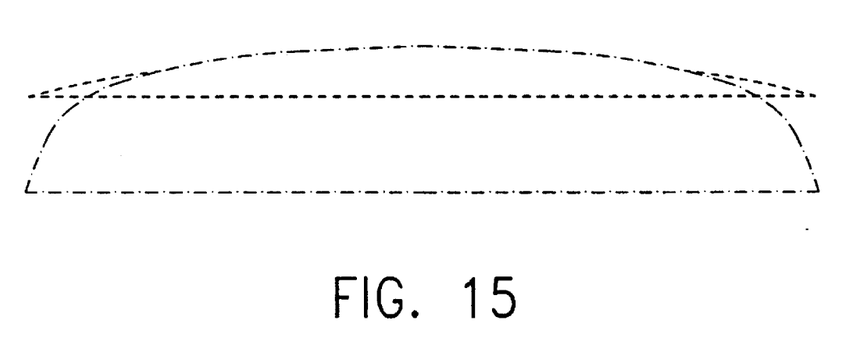
FIG. 15 is a diagrammatic view comparing the lens of FIG. 14 with a simple diopter curve.

FIG. 14 illustrates a further specific embodiment indicated generally by the reference character 56. This lens 56 is an aspheric with a 2.00 diopter central curve with a 14th-order term in the surface generating expression to be outlined hereinbelow. FIG. 15 which compares the shape of the lens 56, indicated in dot-dash lines, with a simple 2.00 diopter curve illustrated in broken lines, makes clear the advantage of the aspheric type in side coverage and in appearance.

Figure 16:
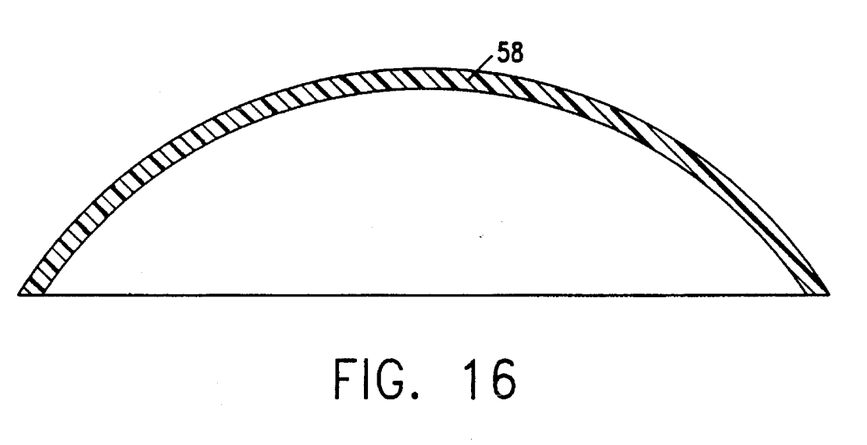
FIG. 16 is a sectional view of another form of my improved lens.
Figure 17:
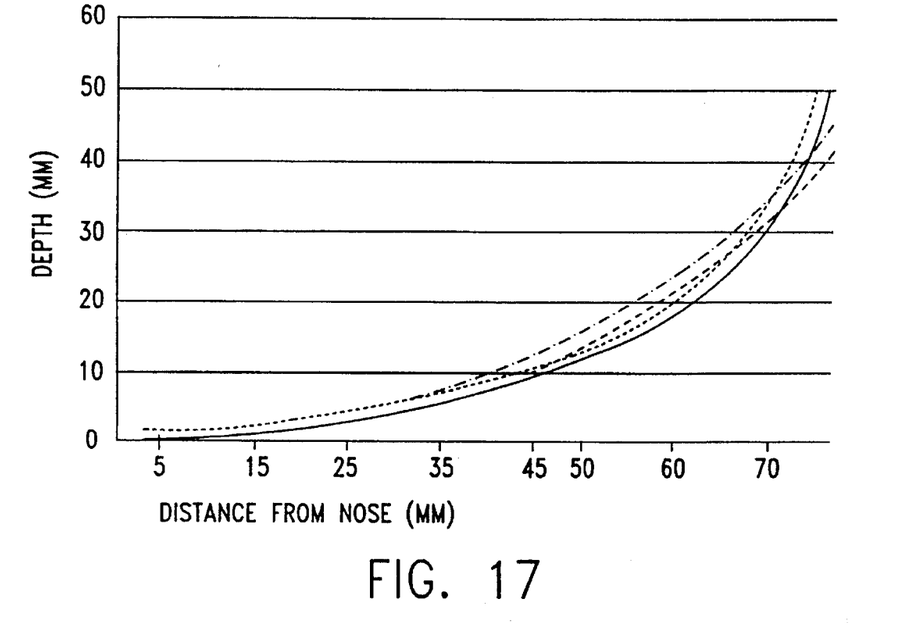
FIG. 17 is a schematic view comparing the lens of FIG. 16 with a simple diopter curve.

FIG. 16 illustrates yet another embodiment indicated generally by the reference character 58 of a lens produced in accordance with my invention. It shows a lens having a central curvature of 6.00 diopters with a 14th-order term in the surface generating expression. FIG. 17 is a graph comparing the design of FIG. 16 with a simple 6.00 diopter curve. In FIG. 17 the full line and the dotted line represent the inner and outer surfaces of the lens 58. The broken line and the dot-dash line represent the inner and outer surfaces of a lens formed with a simple 6.00 diopter curve. While the cosmetic advantages and wrap depth are not as dramatic in this case, the aspheric construction provides for a more uniform thickness than does spherical or toric construction. A spherical lens with a 2.0 mm edge would be 2.9 mm thick in the center. The result would be uneven color across the lens in a sunglass and a heavier than necessary lens.

Figure 18:
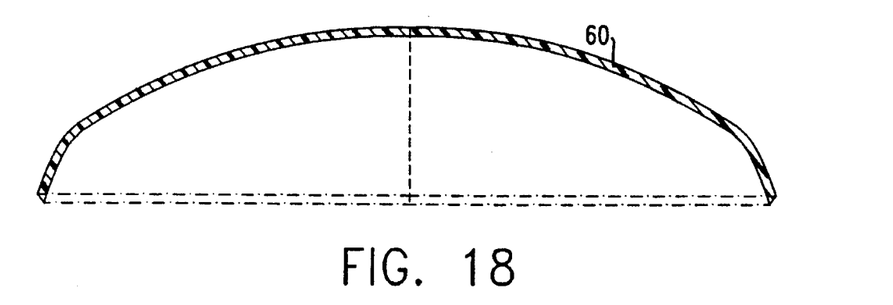
FIG. 18 is a sectional view of yet another form of my improved lens.
Figure 19:
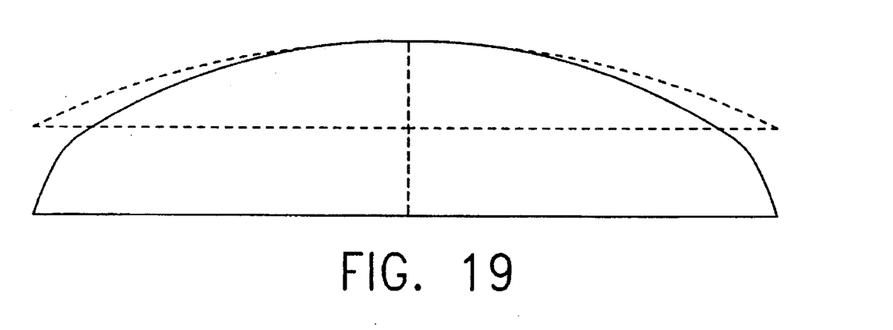
FIG. 19 is a schematic view comparing the lens of FIG. 18 with a simple diopter curve.

FIG. 18 illustrates yet another embodiment 60 of an aspheric lens made in accordance with my invention using oblate spheroids in a manner to be described. FIG. 19 compares the shape of the lens of FIG. 18 with a simple diopter curve.

Figure 20:
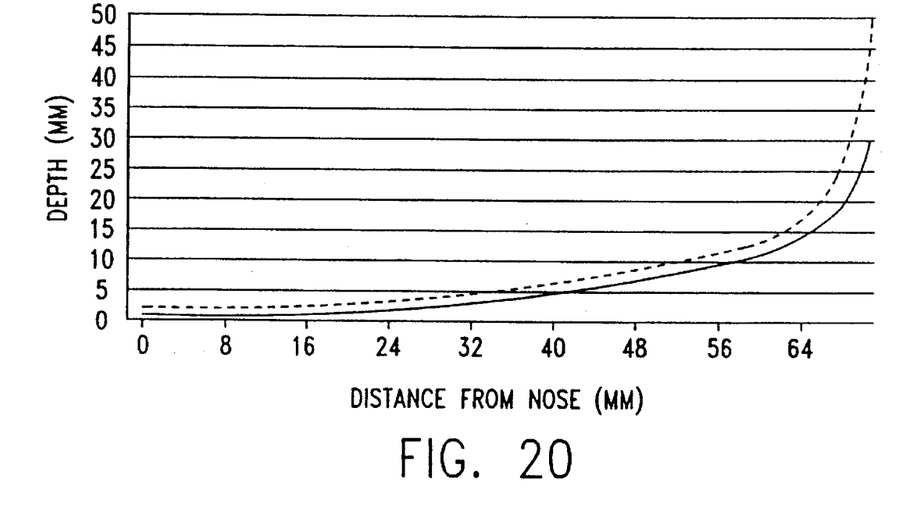
FIG. 20 is a diagram illustrating the configuration of the front and back surfaces of the form of lens shown in FIGS. 6 to 9.

FIG. 20 is a half lens view illustrating the thickness of a deep wrap bi-aspheric sunglass or eye protector with a 3.0 diopter center and a high order exponent of 30.

Figure 21:
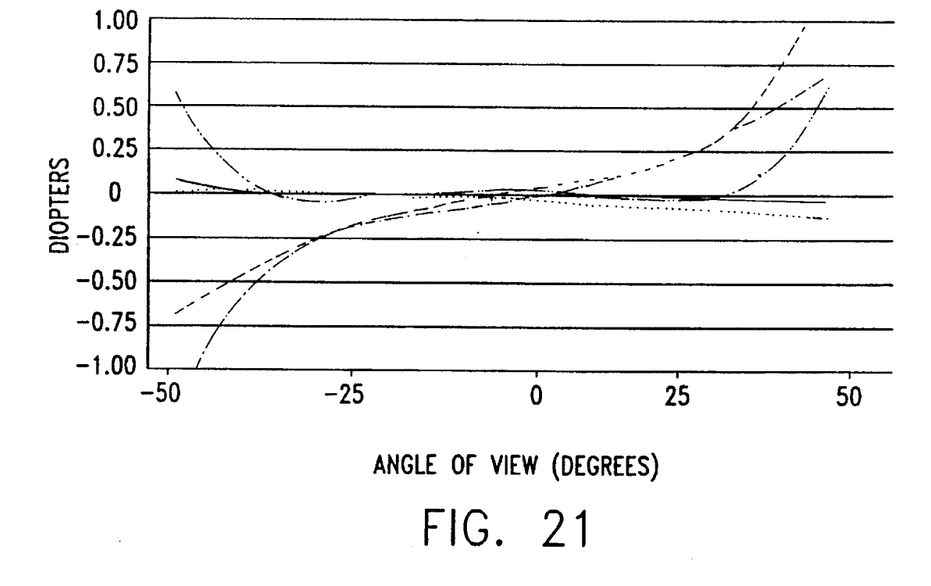
FIG. 21 is a diagram illustrating the optical properties of the lens illustrated in FIGS. 6 to 9.

FIG. 21 illustrates the optical properties of the sunglass or eye protector illustrated in FIG. 20 for a pupillary distance of 64 mm and a center of rotation of 30 mm. In this Figure, as well as the Figures to be described hereinbelow, the dotted line represents tangential right eye power. The solid line represents right eye sagittal power. The broken line represents right eye prism. The dot-dash line represents left eye prism and the dot-dot-dash line represents imbalance.

Figure 22:
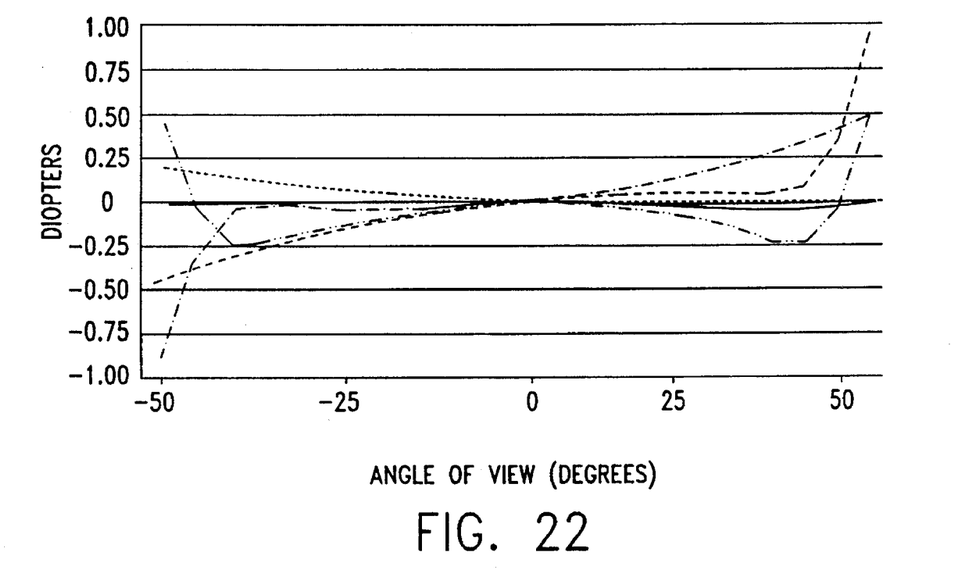
FIG. 22 is a diagram illustrating the optical properties of a lens of the form illustrated in FIGS. 14 and 15.

FIG. 22 shows the optical properties of 2.00 base aspheric sunglass optics having a high order term exponent of 14, a center of rotation of 30 mm and a pupillary distance of 64 mm.

Figure 23:
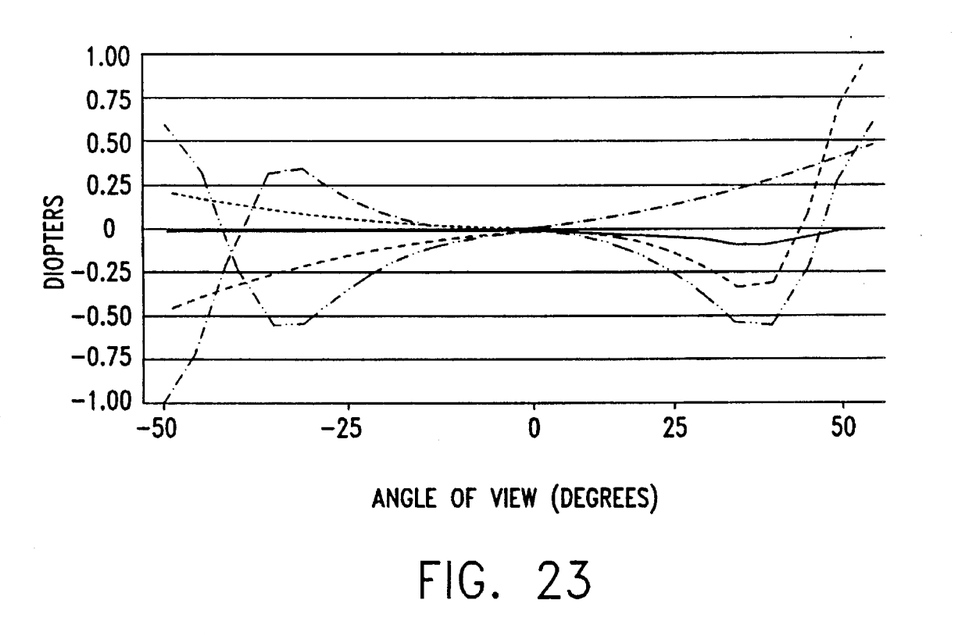
FIG. 23 is a diagram illustrating the optical properties of another lens of the type shown in FIGS. 14 and 15.

FIG. 23 shows the optical properties of 2.00 base aspheric sunglass optics with a high order term exponent of 14, a center of rotation of 35 mm and a pupillary distance of 72 mm.

Figure 24:
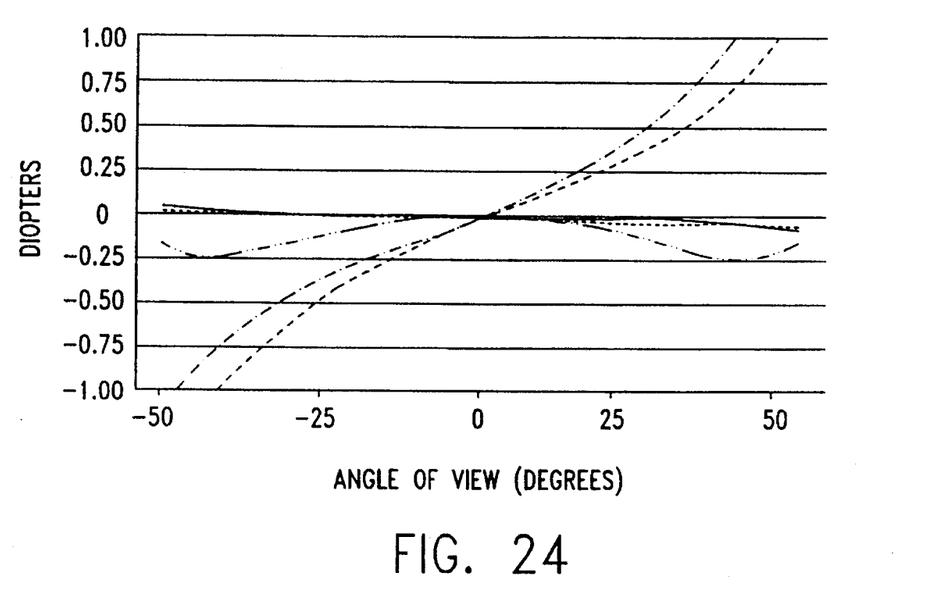
FIG. 24 is a diagram illustrating the optical properties of one form of lens of the type shown in FIGS. 16 and 17.

FIG. 24 shows the optical properties of a 6.00 base (corrected) lens having a high order term exponent of 14, a center of rotation of 30 mm and a pupillary distance of 64 mm.

Figure 25:
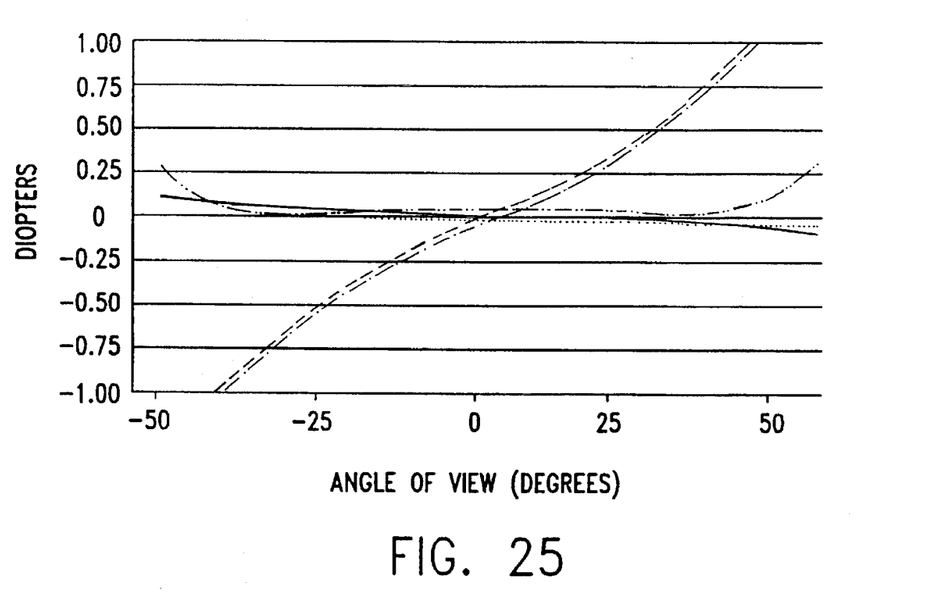
FIG. 25 is a diagram illustrating the optical properties of another lens of the type illustrated in FIGS. 16 and 17.

FIG. 25 shows the optical properties of a lens similar to that to which FIG. 24 relates but having a center of rotation of 35 mm and a pupillary distance of 72 mm.

Figure 26:
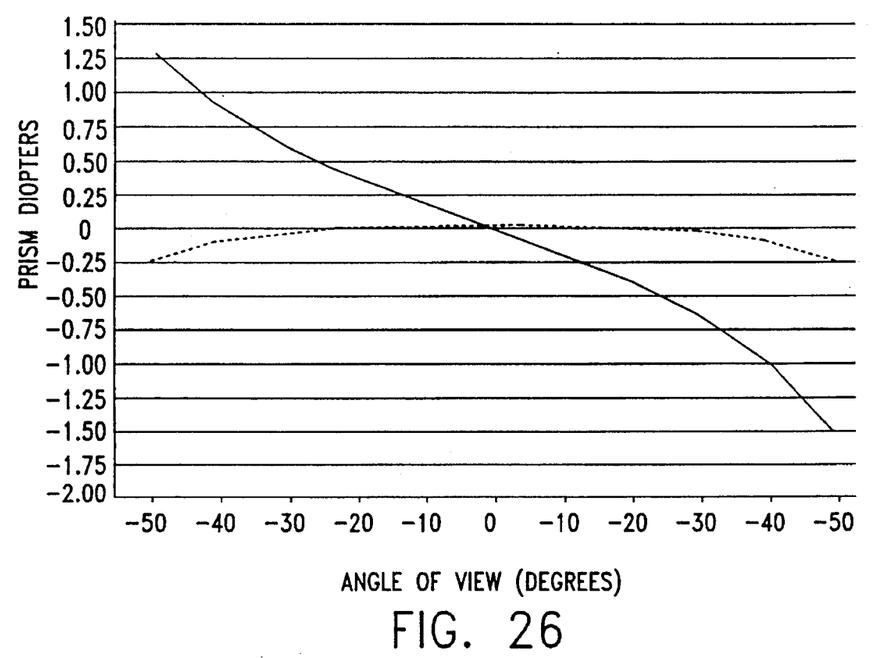
FIG. 26 is a diagram illustrating the prism characteristic of a lens having an oblate ellipsoid surface.

FIG. 26 shows the prism characteristic of a lens having an oblate ellipsoid surface with the dotted line showing imbalance and the full line showing prism.

Figure 27:
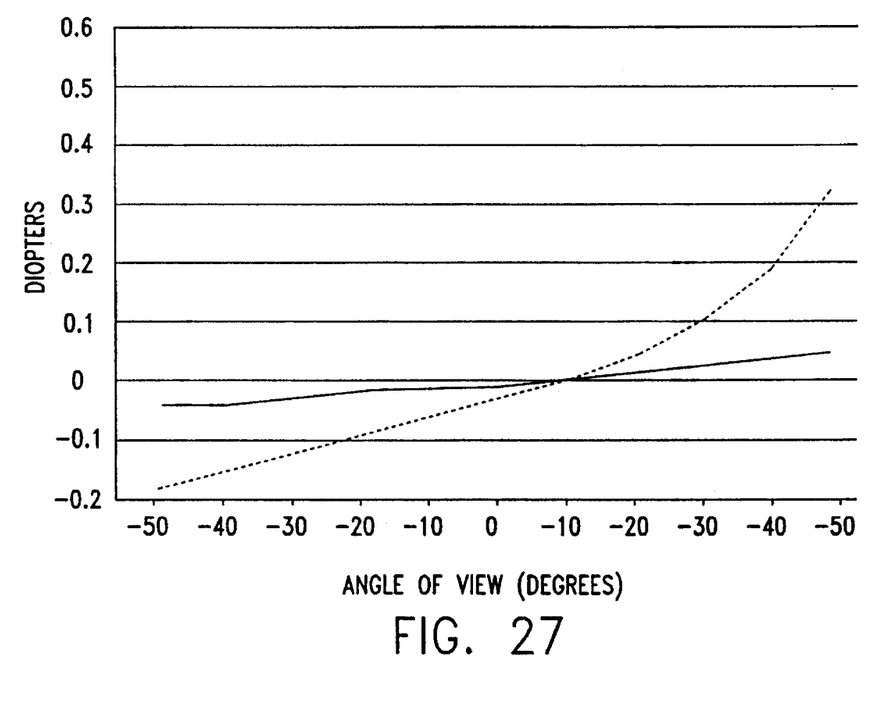
FIG. 27 is a diagram illustrating the power characteristic of the lens to which FIG. 26 relates.

FIG. 27 shows the power characteristic of the lens of FIG. 26 with the dotted line showing saggital power and the full line showing tangential power.

Figure 28:
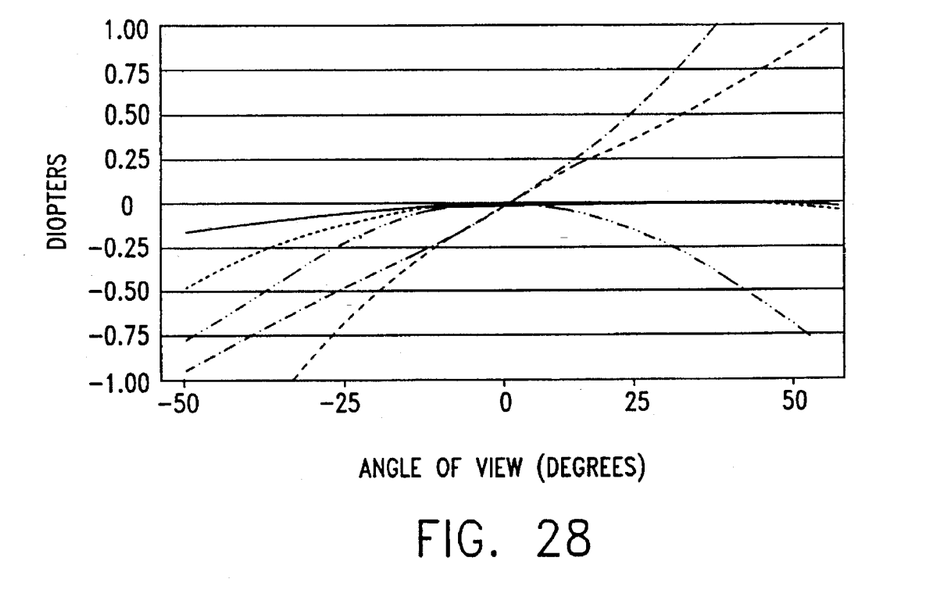
FIGS. 28 to 30 are diagrams illustrating the optical characteristics of spherical lenses for comparison with the aspheric lenses of my invention.

FIG. 28 shows the optical characteristics of a 6.00 base spherical one-piece lens having a 2.7 mm center, 2.0 mm edge thickness, "0" power, and center of rotation 30 mm and pupillary distance of 64 mm.

Figure 29:
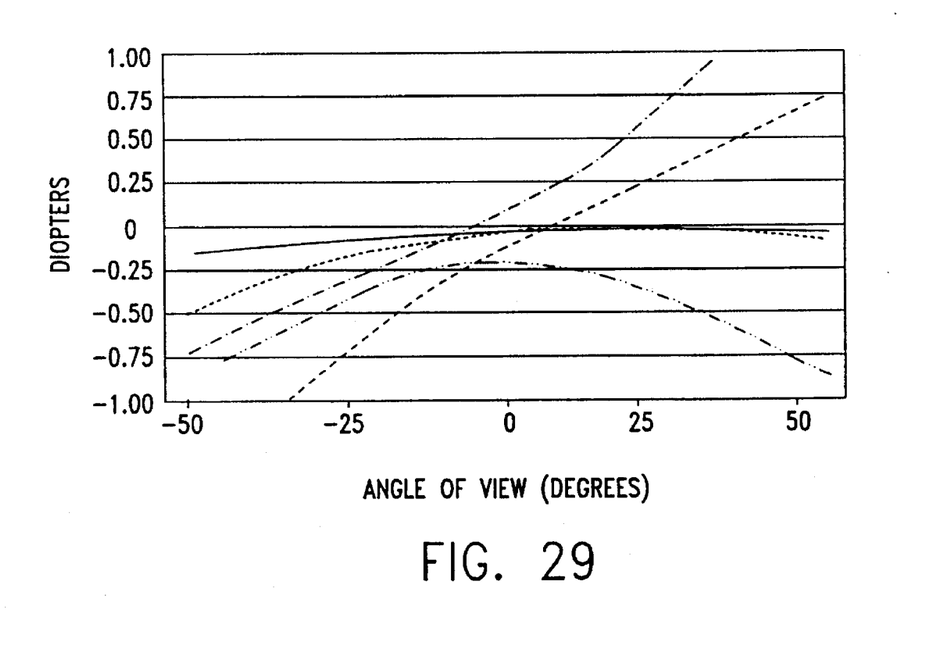

FIG. 29 shows the optical characteristics of a 6.00 base spherical one-piece lens having a 2.5 mm center thickness, 2.0 edge thickness, "−.03" power, a center of rotation 30 mm and pupillary distance of 64 mm.

Figure 30:
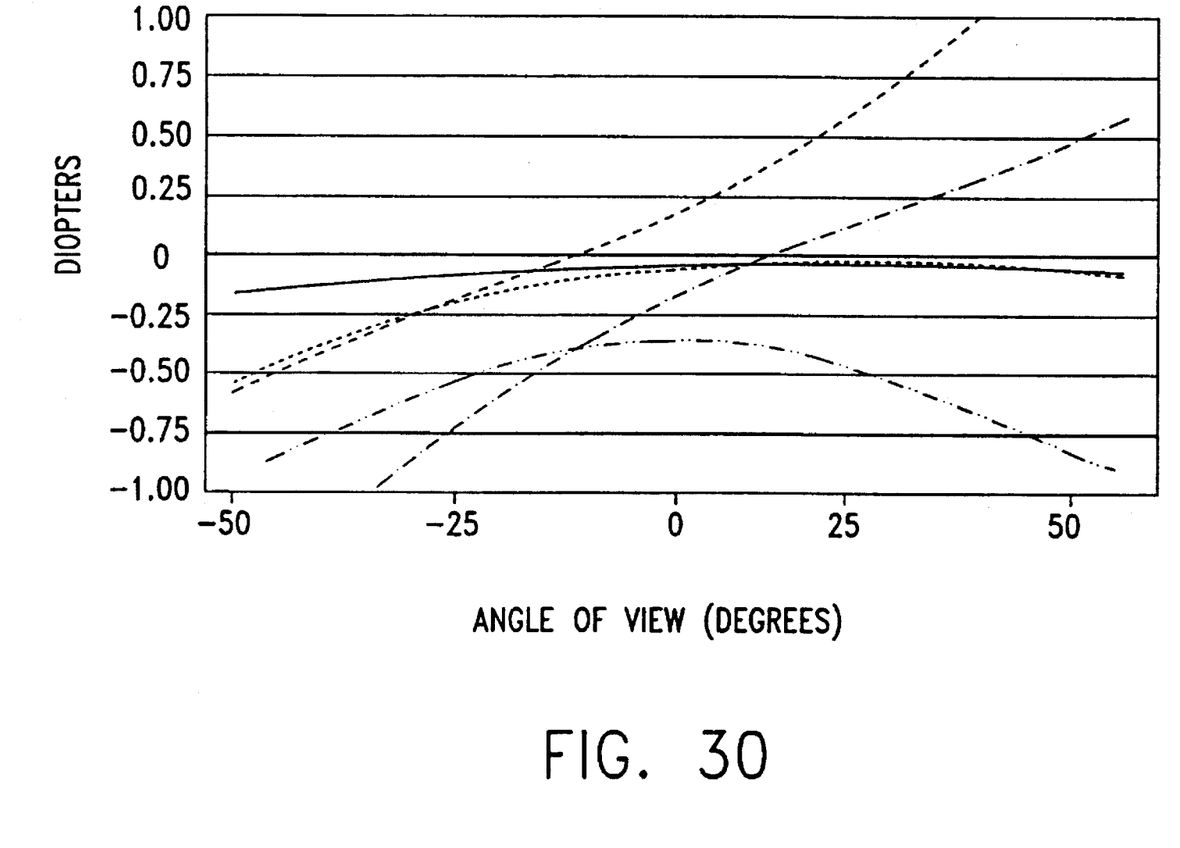

FIG. 30 shows the optical characteristics of a 6.00 base spherical one-piece lens having a 2.3 mm center thickness, 2.0 edge thickness "−0.05" power, a center of rotation of 30 mm and a pupillary distance of 64 mm.

It is to be understood that FIGS. 28 to 30 which relate to spherical lenses are included for comparison purposes.

Table 1 hereinbelow, outlines the optical characteristics of the various forms of lens discussed hereinabove. In the Table base curvature is in diopters, thicknesses are in millimeters, power is in diopters and prism is in prism diopters.

B = the coefficient that controls depth at a specified diamter
C = the exponent that controls abruptness of wrap
D = center thickness in meters and
r = radiate coordinate ($r^2 = x^2 + y^2$)

It will be understood that for the coefficients shown in Table 2 below, the sagitta will be in meters if r is in meters.

TABLE 2

| Type | Surf | A | B | C | D |
|---|---|---|---|---|---|
| Hi Order = 50 | Front | 3.773585 | $5.643593 \times 10^{54}$ | 50 | 0.0000 |
| | Back | 3.794748 | $2.083825 \times 10^{55}$ | 50 | 0.0020 |
| Hi Order = 30 | Front | 2.830189 | $4.822104 \times 10^{32}$ | 30 | 0.0000 |
| | Back | 2.840287 | $8.559449 \times 10^{32}$ | 30 | 0.0017 |
| Hi Order = 30 | Front | 2.830189 | $4.254815 \times 10^{32}$ | 30 | 0.0000 |
| Safety Th | Back | 2.842076 | $9.349795 \times 10^{32}$ | 30 | 0.0020 |
| Hi Order = 14 | Front | 5.660377 | $1.257946 \times 10^{14}$ | 14 | 0.0000 |
| | Back | 5.700915 | $1.683942 \times 10^{14}$ | 14 | 0.0017 |
| Hi Order = 14 | Front | 5.613329 | $1.282143 \times 10^{14}$ | 14 | 0.0000 |
| Safety Th | Back | 5.660377 | $1.808276 \times 10^{14}$ | 14 | 0.0020 |
| Hi Order = 14 | Front | 3.773585 | $7.088609 \times 10^{13}$ | 14 | 0.0000 |
| | Back | 3.791559 | $9.195496 \times 10^{13}$ | 14 | 0.0017 |
| Hi Order = 14 | Front | 3.773585 | $7.088609 \times 10^{13}$ | 14 | 0.0000 |
| Safety Th | Back | 3.794748 | $9.630618 \times 10^{13}$ | 14 | 0.0020 |

The designs shown and described above are developed in the following manner. The designer first selects the desired central curve for either the front or the back curve. He then calculates the wrap depth which that curve provides at the desired outer edge of the lens. Next, the exponent of the high order term and the coefficients are experimentally determined by trial and error to achieve the desired wrap depth, cosmetic appearance and peripheral optical performance. The high order term simply provides the desired wrap depth. Different exponents flatten and steepen the corner and alter the field of view optical performance. Once one of the curves, such as the back curve, is determined, the front curve is calculated to provide zero power or near zero at the center in view of the thickness. The high order term is selected to provide the desired depth at the larger outer diameter.

The procedure described above by itself affords acceptable optical performance. The optics can be improved for

TABLE 1

| | | | | | 0° Angle | | | 20° Angle | | | 40° Angle | | |
|---|---|---|---|---|---|---|---|---|---|---|---|---|---|
| Type | FIG. | Base Curve | Ctr Thick. | Edge Thick. | Power | LE Prism | Prism Imb. | Power | LE Prism | Prism Imb. | Power | LE Prism | Prism Imb. |
| P.A. | 1 | 10 | 2.285 | 1.7 | −0.137 | 0.126 | 0.253 | −0.209 | 0.539 | 0.285 | −0.33 | 0.955 | 0.343 |
| Safety | 1 | 10 | 3.52 | 2 | 0.008 | 0.002 | 0 | −0.12 | 0.972 | 0.097 | −0.364 | 1.99 | 0.3185 |
| P.A. | 2 | 6 | 1.5 | 1 | 0 | 0 | 0 | −0.017 | 0.24 | 0.02 | −0.075 | 0.55 | 0.08 |
| Safety | 2 | 6 | 3.35 | 3 | 0 | 0 | 0 | −0.04 | 0.53 | 0.0047 | −0.163 | 1.208 | 0.182 |
| P.A. | 3 | 3 | 2 | 2 | −0.024 | 0.078 | 0.156 | −0.04 | 0.236 | 0.189 | −0.1 | 0.489 | 0.297 |
| "0" Power | 3 | 3 | 2.11 | 2 | 0 | 0 | 0 | −0.009 | 0.185 | 0.032 | −0.05 | 0.492 | 0.148 |
| Sph., Tor. or Cyl. | 3 | 6 | 2 | 1.7 | −0.118 | 0.29 | 0.58 | −0.22 | 0.628 | 0.669 | −0.43 | 1.056 | 0.87 |
| Safety | 3 | 6 | 2 | 2 | −0.133 | 0.328 | 0.655 | −0.245 | 0.658 | 0.74 | −0.458 | 1.066 | 0.928 |
| Asph. (14) | 4,5 | 6 | 1.7 | 1.7 | −0.008 | 0.006 | 0.013 | −0.048 | 0.305 | 0.141 | −0.156 | 0.83 | 0.535 |
| Safety | 4,5 | 6 | 2 | 2 | −0.01 | 0.007 | 0.015 | −0.058 | 0.356 | 0.164 | −0.181 | 0.967 | 0.623 |
| Asph (30) | 4,5 | 3 | 1.7 | 1.5 | 0 | 0 | 0 | −0.007 | 0.146 | 0.033 | −0.052 | 0.398 | 0.155 |
| Safety | 4,5 | 3 | 2 | 2 | 0 | 0 | 0 | −0.008 | 0.172 | 0.039 | −0.096 | 0.467 | 0.188 |
| Asph (50) | | 4 | 2 | 2 | −0.001 | 0.001 | 0.003 | −0.014 | 0.233 | 0.07 | −0.08 | 0.632 | 0.299 |

The sagitta z of the aspheric lenses identified in Table I is given by the relationship $$z = Ar^2 + Br^c + D$$

where

A = the coefficient that governs vertex curvature certain interpupillary distances by adding other polynomial terms to the front surface, back surface or both. Thus, the front surface may have terms of exponents 2, 4, 6 and 8 plus a high order term which can range from 8 to 30.

Conic sections can also be used. For example, in the embodiment 60 illustrated in FIG. 18, a pair of oblate ellipsoids are used. The front surface has a vertex curvature of 3.7857 D (1.53) and a shape factor of 4.00. Shape factor is the same as one minus the square of the eccentricity where the eccentricity can be either a real or an imaginary number. The back surface has a vertex curvature of 3.8147 D (1.53) and a shape factor of 4.09. Combined at a center thickness of 3 mm using a material having an index of refraction of 1.586, the resulting lens has essentially zero optical power at the vertex and a caliper edge thickness of about 1.3 mm at a diameter of 140 mm. At this diameter, the wrap depth is 35 mm because the major and minor axes of the cross-section ellipse are in the ratio of 2/1. It follows that the tangents at each extreme edge are at right angles to the tangent at the vertex. FIG. 19 compares this lens with a simple spherical 3.7857 D (1.53) curve. The advantages of the lens of FIG. 18 are obvious.

It will be seen that I have accomplished the objects of my invention. I have provided improved molded sunglasses and eyeglasses which afford a greater freedom of cosmetic design. My improved sunglasses and eyeglasses are of substantially uniform thickness throughout without sacrificing optical performance. I have provided safety glasses and eye shields with integral side protection in one continuous optical surface with an unbroken side wrap with sufficient thickness to meet safety standards and to provide high quality optics through a wide field of view.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention, what we claim is:

1. A sunglass or eye protector molded from suitable optical material with inner and outer surfaces, both of said surfaces being continuously curved and noncircular in the horizontal direction to provide substantially uniform thickness throughout and having wrap depth or rearwardly extending portions generally along the side of the head of a wearer and being curved in the vertical meridian, both surfaces being figures of revolution the curvatures of which are generated by conic sections.

2. A sunglass or eye protector molded from suitable optical material with inner and outer surfaces, both of said surfaces being continuously curved and noncircular in the horizontal direction to provide substantially uniform thickness throughout and having wrap depth or rearwardly extending portions generally along the side of the head of a wearer and being curved in the vertical meridian, the curvatures of both surfaces being generated by a 2nd-order term imparting a 3.00 D(1.53) vertex curve combined with a 30th-order term where 1.53 is the standard assumed index of refraction used to describe curvature in the optical industry.

3. A sunglass or eye protector as in claim 2 in which the axis of revolution being the optical axis of the protector providing a rotationally symmetrical protector having the same cross section in all meridians.

4. A sunglass or eye protector as in claim 2, the axis of revolution being a horizontal line at 90 degrees to the optical axis and having a radius of curvature longer than the wrap depth, thus providing an atoric symmetrical protector to have a non-circular cross section in the horizontal meridian and circular cross sections in the vertical meridian.

5. A sunglass or eye protector as in claim 2 comprising a pair of separate lenses.

6. A sunglass or eye protector as in claim 2 comprising a single axis eye protector.

7. A sunglass or eye protector molded from suitable optical material with inner and outer surfaces, both of said surfaces being continuously curved and noncircular in the horizontal direction to provide substantially uniform thickness and having wrap depth or rearwardly extending portions generally along the side of the head of a wearer and being curved in the vertical meridian, the curvatures of both surfaces being generated by a 2nd-order term imparting a 4.00 D(1.53) vertex curve combined with a 14th-order term where 1.53 is the standard assumed index of refraction used to describe curvature in the optical industry.

8. A sunglass or eye protector as in claim 7, the axis of revolution being the optical axis of the protector providing a rotationally symmetrical protector having the same cross section in all meridians.

9. A sunglass or eye protector as in claim 7, the axis of revolution being a horizontal line at 90 degrees to the optical axis and having a radius of curvature longer than the wrap depth, thus providing an atoric symmetrical protector having a non-circular cross section in the horizontal meridian and circular cross sections in the vertical meridian.

10. A sunglass or eye protector as in claim 7 comprising a pair of separate lenses.

11. A sunglass or eye protector as in claim 7 comprising a single axis eye protector.

12. A sunglass or eye protector molded from suitable optical material with inner and outer surfaces, both of said surfaces being continuously curved and non-circular in the horizontal direction to provide substantially uniform thickness throughout and having wrap depth or rearwardly extending portions generally along the side of the head of a wearer and being curved in the vertical meridian, the curvatures of both surfaces being generated by a 2nd-order term imparting a 6.00 D(1.53) vertex curve combined with a 14th-order term where 1.53 is the standard assumed index of refraction used to describe curvature in the optical industry.

13. A sunglass or eye protector as in claim 12, the axis of revolution being the optical axis of the protector providing a rotationally symmetrical protector having the same cross section in all meridians.

14. A sunglass or eye protector as in claim 12, the axis of revolution being a horizontal line at 90 degrees to the optical axis and having a radius of curvature longer than the wrap depth, thus providing an atoric symmetrical protector having a non-circular cross section in the horizontal meridian and circular cross sections in the vertical meridian.

15. A sunglass or eye protector as in claim 12, comprising a pair of separate lenses.

16. A sunglass or eye protector as in claim 12 comprising a single axis eye protector.

17. A sunglass or eye protector molded from suitable optical material with inner and outer surfaces, both of said surfaces being continuously curved and noncircular in the horizontal direction to provide substantially uniform thickness throughout and having wrap depth or rearwardly extending portions generated along the side of the head of a wearer and being curved in the vertical meridian, both surfaces being oblate ellipsoids.

18. An aspheric sunglass or eyeshield having inner and outer surfaces, the transverse curvatures in the center regions of which lie between 1.0 and 6 diopters in combination with other polynomial terms having exponents between 10 and 30.

19. A sunglass or eye protector as in claim 18 comprising a pair of separate lenses.

20. A sunglass or eye protector as in claim 18 comprising a single axis eye protector.

21. An aspheric sunglass or eye shield having inner and outer aspheric surfaces providing substantially uniform thickness throughout, said sunglass or eyeshield having the performance and description of one of the lens types set forth in the following table:

| Type | FIG. | Base Curve | Ctr Thick. | Edge Thick. | 0° Angle | | | 20° Angle | | | 40° Angle | | |
|---|---|---|---|---|---|---|---|---|---|---|---|---|---|
| | | | | | Power | LE Prism | Prism Imb. | Power | LE Prism | Prism Imb. | Power | LE Prism | Prism Imb. |
| Asph. (14) | 4,5 | 6 | 1.7 | 1.7 | −0.008 | 0.006 | 0.013 | −0.048 | 0.305 | 0.141 | −0.156 | 0.83 | 0.535 |
| Safety | 4,5 | 6 | 2 | 2 | −0.01 | 0.007 | 0.015 | −0.058 | 0.356 | 0.164 | −0.181 | 0.967 | 0.623 |
| Asph (30) | 4,5 | 3 | 1.7 | 1.5 | 0 | 0 | 0 | −0.007 | 0.146 | 0.033 | −0.052 | 0.398 | 0.155 |
| Safety | 4,5 | 3 | 2 | 2 | 0 | 0 | 0 | −0.008 | 0.172 | 0.039 | −0.096 | 0.467 | 0.188 |
| Asph (50) | 4 | 2 | 2 | −0.001 | 0.001 | 0.003 | −0.014 | 0.233 | 0.07 | −0.08 | 0.632 | 0.299 |

22. An aspheric sunglass or eye shield as in claim 21 in which the sagitta of the surfaces are given by the relationship $$z = Ar^2 + Br^c + D$$

where

A = the coefficient that governs vertex curvature

B = the coefficient that controls depth at a specified diameter

C = the exponent that controls abruptness of wrap

D = center of thickness in meters and r = radiate coordinate ($r^2 = x^2 + y^2$)

and where A, B, C, D and r have production specifications given by the following table for said one lens type:

| Type | Surf | A | B | C | D |
|---|---|---|---|---|---|
| Hi Order = 50 | Front | 3.773585 | 5.643593 × 10$^{54}$ | 50 | 0.0000 |
| | Back | 3.794748 | 2.083825 × 10$^{55}$ | 50 | 0.0020 |
| Hi Order = 30 | Front | 2.830189 | 4.822104 × 10$^{32}$ | 30 | 0.0000 |
| | Back | 2.840287 | 8.559449 × 10$^{32}$ | 30 | 0.0017 |
| Hi Order = 30 | Front | 2.830189 | 4.254815 × 10$^{32}$ | 30 | 0.0000 |
| Safety Th | Back | 2.842076 | 9.349795 × 10$^{32}$ | 30 | 0.0020 |
| Hi Order = 14 | Front | 5.660377 | 1.257946 × 10$^{14}$ | 14 | 0.0000 |
| | Back | 5.700915 | 1.683942 × 10$^{14}$ | 14 | 0.0017 |
| Hi Order = 14 | Front | 5.613329 | 1.282143 × 10$^{14}$ | 14 | 0.0000 |
| Safety Th | Back | 5.660377 | 1.808276 × 10$^{14}$ | 14 | 0.0020 |
| Hi Order = 14 | Front | 3.773585 | 7.088609 × 10$^{13}$ | 14 | 0.0000 |
| | Back | 3.791559 | 9.195496 × 10$^{13}$ | 14 | 0.0017 |
| Hi Order = 14 | Front | 3.773585 | 7.088609 × 10$^{13}$ | 14 | 0.0000 |
| Safety Th | Back | 3.794748 | 9.630618 × 10$^{13}$ | 14 | 0.0020 |

23. An aspheric sunglass or eye shield having inner and outer aspheric surfaces providing substantially uniform thickness throughout, the sagitta of said surfaces being given by the relationship $$z = Ar^2 + Br^c + D$$

where

A = the coefficient that governs vertex curvature

B = the coefficient that controls depth at a specified diameter

C = the exponent that controls abruptness of wrap

D = center thickness in meters and r = radiate coordinate ($r = x^2 + y$)

and where A, B, C, D and r have production specifications given by the following table for one of the lens types:

| Type | Surf | A | B | C | D |
|---|---|---|---|---|---|
| Hi Order = 50 | Front | 3.773585 | 5.643593 × 10$^{54}$ | 50 | 0.0000 |
| | Back | 3.794748 | 2.083825 × 10$^{55}$ | 50 | 0.0020 |
| Hi Order = 30 | Front | 2.830189 | 4.822104 × 10$^{32}$ | 30 | 0.0000 |
| | Back | 2.840287 | 8.559449 × 10$^{32}$ | 30 | 0.0017 |
| Hi Order = 30 | Front | 2.830189 | 4.254815 × 10$^{32}$ | 30 | 0.0000 |
| Safety Th | Back | 2.842076 | 9.349795 × 10$^{32}$ | 30 | 0.0020 |
| Hi Order = 14 | Front | 5.660377 | 1.257946 × 10$^{14}$ | 14 | 0.0000 |
| | Back | 5.700915 | 1.683942 × 10$^{14}$ | 14 | 0.0017 |
| Hi Order = 14 | Front | 5.613329 | 1.282143 × 10$^{14}$ | 14 | 0.0000 |
| Safety Th | Back | 5.660377 | 1.808276 × 10$^{14}$ | 14 | 0.0020 |
| Hi Order = 14 | Front | 3.773585 | 7.088609 × 10$^{13}$ | 14 | 0.0000 |
| | Back | 3.791559 | 9.195496 × 10$^{13}$ | 14 | 0.0017 |
| Hi Order = 14 | Front | 3.773585 | 7.088609 × 10$^{13}$ | 14 | 0.0000 |
| Safety Th | Back | 3.794748 | 9.630618 × 10$^{13}$ | 14 | 0.0020 |

\* \* \* \* \*

UNITED STATES PATENT AND TRADEMARK OFFICE
CERTIFICATE OF CORRECTION

PATENT NO. : 5,604,547
DATED      : February 18, 1997
INVENTOR(S): John K. Davis and Richard P. Waido It is certified that error appears in the above-identified patent and that said Letters Patent is hereby corrected as shown below:

Column 7, Claim 3, line 1, delete "in which" and substitute --,--.

Column 7, Claim 4, lines 4 and 5, delete "to have" and substitute --having--.

Column 10, Claim 23, line 25, within the parenthesis, change "r" to $--r^2--$ and "y" to $--y^2--$.

Signed and Sealed this

Twenty-eighth Day of October, 1997

Attest:

BRUCE LEHMAN

Attesting Officer

Commissioner of Patents and Trademarks